United States Patent [19]

Steer

[11] Patent Number: 4,636,205

[45] Date of Patent: Jan. 13, 1987

[54] OSTOMY BAG MAGNETIC COUPLING

[75] Inventor: Peter L. Steer, Surrey, England

[73] Assignee: Craig Medical Products Limited, Surrey, England

[21] Appl. No.: 659,936

[22] Filed: Oct. 11, 1984

[30] Foreign Application Priority Data

Oct. 13, 1983 [GB] United Kingdom ............... 8327469

[51] Int. Cl.⁴ .............................................. A61F 5/44
[52] U.S. Cl. .................................................. 604/338
[58] Field of Search .............................. 604/332–345; 252/62.63; 273/235

[56] References Cited

U.S. PATENT DOCUMENTS

| 3,565,073 | 2/1971 | Giesy | 604/343 |
| 3,952,726 | 4/1976 | Hennig et al. | 128/DIG. 25 |
| 4,154,226 | 5/1979 | Hennig et al. | 128/283 |
| 4,205,678 | 6/1980 | Adair | 128/283 |
| 4,210,132 | 7/1980 | Perlin | 128/DIG. 25 |
| 4,258,705 | 3/1981 | Sorensen et al. | 128/283 |
| 4,411,807 | 10/1983 | Watanabe et al. | 252/62.63 |
| 4,518,389 | 5/1985 | Steer et al. | 604/339 |

FOREIGN PATENT DOCUMENTS

| 2514285 | 10/1976 | Fed. Rep. of Germany | 604/335 |
| 2648222 | 4/1978 | Fed. Rep. of Germany | 604/332 |
| 2031282 | 4/1980 | United Kingdom . | |
| 1568860 | 6/1980 | United Kingdom . | |
| 1571657 | 7/1980 | United Kingdom . | |
| 1579875 | 11/1980 | United Kingdom . | |
| 1583027 | 1/1981 | United Kingdom . | |
| 1586823 | 3/1981 | United Kingdom . | |
| 1586824 | 3/1981 | United Kingdom . | |
| 1595906 | 8/1981 | United Kingdom . | |
| 1596047 | 8/1981 | United Kingdom . | |
| 2115288 | 9/1983 | United Kingdom . | |

Primary Examiner—C. Fred Rosenbaum
Assistant Examiner—J. L. Kruter
Attorney, Agent, or Firm—Lawrence S. Levinson; Sanford J. Asman

[57] ABSTRACT

A two part coupling for joining an ostomy bag to a pad or to a faceplate is characterized in that the two cooperating coupling parts are held together in a detachable manner by magnetic force.

6 Claims, 1 Drawing Figure

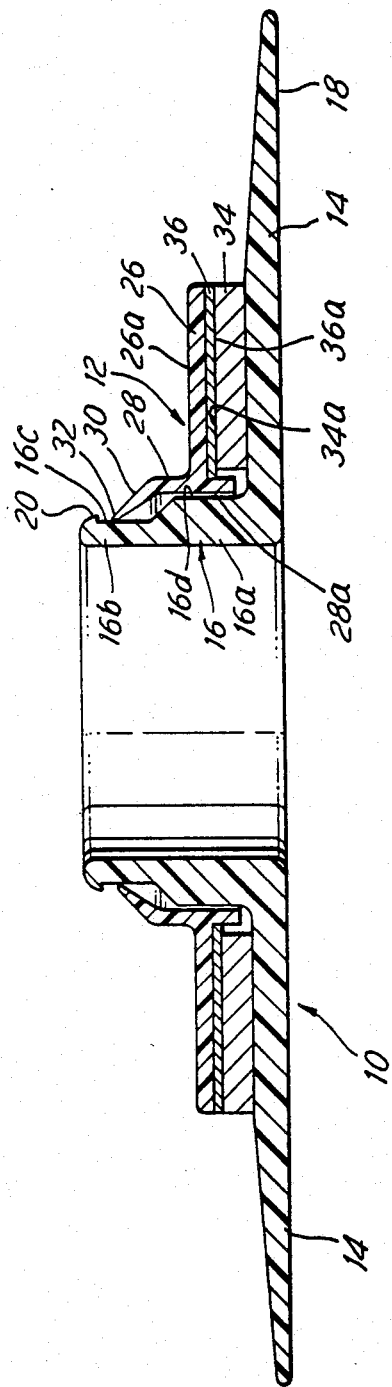

OSTOMY BAG MAGNETIC COUPLING

BACKGROUND OF THE INVENTION

This invention relates to an ostomy bag coupling.

It has become the currently preferred practice for ostomy bags to be detachably secured to a pad or dressing which contacts the skin of the wearer. Often such a pad or dressing is attached to the wearer by a medical grade adhesive, so dispensing with the inconvenient and uncomfortable belts or harnesses. One successful method of securing an ostomy bag to a pad is described and claimed in British Pat. No. 1571657. The reader is also referred to British Pat. Nos. 1583027, 1586823, 1586824, 1568860, 1579875, 1596047, 1595906, 2031282, and British application No. 2115288A.

Interengaging plastics coupling rings have proved very successful, but one of their disadvantages is that when engaged the resulting coupling has a stiffness which may sometimes lead to discomfort for the wearer.

SUMMARY OF THE INVENTION

According to the present invention, there is provided a two part coupling for joining an ostomy bag to a pad or face plate characterized in that the two cooperating coupling parts are each held together in a detachable manner by magnetic force.

In a preferred embodiment of the invention, each of the cooperating coupling parts has a substantially planar annular surface facing towards the other, and these surfaces are held together by the magnetic force.

One coupling part may carry a permanent magnet and the other coupling part may carry one or more members of ferro-magnetic material. Alternatively there may be one or more permanent magnets on each coupling part. For example, disc magnets may be used, spaced around the central axis of the ostomy bag coupling. One may alternatively employ a flexible bonded magnetic sheet, such as may for example be obtained from James Neill, Napier Street, Sheffield, England.

In a preferred embodiment of the invention, the body side coupling part is formed by a thin flexible radially extending flange and a tubular portion which extends away form the body of the wearer, these may be integral or may be secured together in any convenient way. The whole part may be molded from plastics material. The flange carries on its side further from the body of the wearer an annular flexible magnetic sheet for example a sheet consisting of a fine magnetic powder such as barium ferrite loaded into a thermoplastic binder, the resulting composition having then been calendered into sheet and suitably magnetized. The bag side coupling part for cooperation with the body side coupling part described may then consist of a tubular portion which fits over the tubular portion of the body side coupling part, optionally with a flexible sealing skirt extending inwardly towards the body side coupling part, and also having a radially extending flexible annular flange to which an ostomy bag is secured in any conventional way. The side of this flange facing towards the body of the wearer then carries a flexible sheet of plastics material impregnated with a ferromagnetic material, or alternatively carries a further flexible magnetic sheet.

An important advantage of using magnetic force to secure the two coupling parts together is that this force is strong when the sheets are fully in contact with each other, but once separated in one area, the sheets can easily be pulled apart by the application of a relatively small force, utilizing a "peeling" action.

BRIEF DESCRIPTION OF THE DRAWING

One non-limiting example of the invention will now be described with reference to the accompanying drawing, which is an axial cross-section through one example of coupling according to the invention, shown with the coupling parts in engagement with each other.

DETAILED DESCRIPTION OF THE DRAWING

The illustrated coupling includes a body-side coupling part 10 and bag-side coupling part 12. The body-side coupling part 10 includes a radially extending flexible flange 14 and a central tubular portion 16. These may be molded integrally from synthetics plastics material or may be secured together in any convenient manner. The annular flange 14 has a flat surface 18 facing towards the body of the wearer, upon which can be placed a medical grade adhesive so that the body-side coupling part is secured to the skin of the wearer in the peristomal region. The tubular portion 16 has a part of thicker wall thickness 16a and a part of thinner wall thickness 16b. At the outer end, that is to say the end further from the wearer, there may be an upstanding rib or peripheral series of pips 20. The purpose of these will be later described.

The bag-side coupling element 12 has a radially extending annular flange 26 and a tubular portion 28. The tubular portion 28 is attached to or integral with a tapering flexible deflectable sealing skirt 30 whose tip 32, when the two coupling parts are assembled together, is in contact with the outer cylindrical surface 16c of the tubular portion 16.

An annular magnetic sheet 34 is attached to or forms part of the body-side coupling element 10, and a magnetic sheet 36 is attached to or forms part of the bag-side coupling part 12. Both the sheets 34 and 36 are flexible and while for ease of illustration they have been depicted as of substantial thickness, in practice quite thin sheets may be used. Alternatively, one or other of these magnetic sheets may be of unmagnetised ferromagnetic material or may be of a plastics material impregnated with ferromagnetic powder.

The body-side coupling part has an outer substantially cylindrical surface 16d and the bag-side coupling part 12 as an inner substantially cylindrical surface 28a. The internal diameter of the surface 28a is chosen to be slightly greater than the outside diameter of the surface 16d. The cooperation of these two substantially cylindrical surfaces ensures that the confronting faces 34a and 36a of the sheets 34, 36 meet in a face to face manner as the coupling parts 10 and 12 are assembled together. The flexible sealing skirt 30 stretches slightly to pass over the rib 20 as this assembly is carried out, and then reverts to its normal unstretched condition whereat the tip 32 is in contact with the substantially cylindrical surface 16c. This arrangement provides a mechanical security against inadvertent disassembly of the two coupling parts, as well as a liquid seal.

A conventional ostomy bag is attached to the bag-side coupling 12, for example by a plastics welding operation whereby one of the walls of the bag, having a stomal orifice, is welded or otherwise attached to the surface 26a of the flange 26.

An advantage of the construction illustrated is that the tubular portion 16 acts as a guidance chute and presents a smooth surface to any discharged waste matter, conducting it to the interior of the bag. There are no crevices or cracks or gaps which may become clogged with waste material and thus present a difficult and unpleasant cleaning problem.

It will be appreciated that modifications can be made without departing from the invention. For example either or both of the sheets 34, 36 could be replaced by a peripheral series of flat discs or flat pads, at least some of which are magnetized and cooperate with confronting discs or pads which are either also magnetized or have a ferromagnetic property such that they are magnetically attracted to the confronting pad or disc.

While it is highly desirable that the sheets 34 and 36 should be flexible, this is not essential since adequate flexibility of the body-side coupling flange 14 could be achieved by utilizing small rigid magnetic members suitably located. As another alternative, the magnetic material could be powdered material contained in a suitable groove or chamber integrally molded as part of one or other of the body-side coupling part and the bag-side coupling part.

Other modifications are possible; for example the magnetic force could be produced by an electrical coil embedded in one of the coupling parts, powered by a miniature long life battery. Said battery could be carried by or form part of the ostomy bag coupling or could be carried by the wearer.

As an advantageous feature of the invention, one or both of the magnetic sheets 34, 36 could have a radially projecting tab so that the wearer can readily grip these tabs to start the peeling action when it is desired to separate the bag-side coupling part together with the bag from the body-side coupling part, for example when it is desired to change the bag.

I claim:

1. A coupling for joining an ostomy bag to a pad or face plate comprising:
    a body-side coupling part having a radially extending substantially planar annular surface and a tubular portion which extends away from the body of the wearer, said tubular portion comprising a thicker wall portion connected to a thinner wall portion; and
    a bag-side coupling part having a tubular portion which is adapted for mating engagement with and fits over said body-side tubular portion and a radially extending substantially planar annular surface which is held together with said body-side annular surface by a magnetic sheet means providing magnetic forces when said coupling parts are matingly engaged, said bag-side coupling part further comprising a flexible sealing skirt coupled to said bag-side tubular portion and extending inwardly to engage the thinner wall portion of said body-side tubular portion, said thinner wall portion comprising a projection means over which the flexible sealing strip is deflected when the coupling parts are engaged for providing mechanical security against inadvertent disassembly of the coupling parts, whereby a liquid seal is provided.

2. The invention of claim 1 wherein said magnetic sheet means comprise by a permanent magnetic material carried by one of said bag-side or body-side annular surfaces and ferromagnetic material carried by the other, whereby said bag-side and body-side annular surfaces are held together by magnetic forces when said coupling parts are matingly engaged.

3. The invention of claim 2 wherein said permanent magnetic material comprises a flexible magnetic sheet bonded to said body-side coupling part and said ferromagnetic material comprises a flexible sheet of plastic material impregnated with ferromagnetic material bonded to said bag-side coupling part.

4. The invention of claim 3 wherein said flexible magnetic sheet comprises a fine magnetic powder including barium ferrite loaded into a thermoplastic binder.

5. The invention of claim 2 wherein said permanent magnetic material comprises a flexible magnetic sheet bonded to said bag-side coupling part and said ferromagnetic material comprises a flexible sheet of plastic material impregnated with ferromagnetic material bonded to said body-side coupling part.

6. The invention of claim 5 wherein said flexible magnetic sheet comprises a fine magnetic powder including barium ferrite loaded into a thermoplastic binder.

* * * * *